United States Patent [19]

Kelm et al.

[11] Patent Number: 5,914,132
[45] Date of Patent: *Jun. 22, 1999

[54] PHARMACEUTICAL DOSAGE FORM WITH MULTIPLE ENTERIC POLYMER COATINGS FOR COLONIC DELIVERY

[75] Inventors: Gary Robert Kelm, Cincinnati, Ohio; Koji Kondo; Akio Nakajima, both of Kobe, Japan

[73] Assignee: The Procter & Gamble Company, Cincinnati, Ohio

[*] Notice: This patent is subject to a terminal disclaimer.

[21] Appl. No.: 08/728,946

[22] Filed: Oct. 11, 1996

Related U.S. Application Data

[63] Continuation-in-part of application No. 08/442,920, May 17, 1995, Pat. No. 5,686,105, and application No. 08/442,914, May 17, 1995, Pat. No. 5,656,290, which is a continuation-in-part of application No. 08/279,361, Jul. 22, 1994, abandoned, which is a continuation of application No. 08/023,412, Feb. 26, 1993, abandoned.

[51] Int. Cl.⁶ .............................. A61K 9/44; A61K 9/32; A61K 9/40
[52] U.S. Cl. .................. 424/478; 424/467; 424/475; 424/479; 424/481; 424/482
[58] Field of Search .................... 424/489, 490, 424/497, 482

[56] References Cited

U.S. PATENT DOCUMENTS

| | | | |
|---|---|---|---|
| 2,764,590 | 9/1956 | Kottler et al. | |
| 3,431,338 | 3/1969 | Munzel | 424/21 |
| 4,432,966 | 2/1984 | Zeitoun et al. | 424/21 |
| 4,816,259 | 3/1989 | Matthews et al. | 424/463 |
| 4,822,629 | 4/1989 | Pong | 424/480 |
| 4,834,985 | 5/1989 | Elger et al. | 424/488 |
| 4,910,021 | 3/1990 | Davis et al. | 424/456 |
| 4,952,402 | 8/1990 | Sparks et al. | 424/419 |
| 5,068,110 | 11/1991 | Fawzi et al. | 424/461 |
| 5,171,580 | 12/1992 | Iamartino et al. | 424/490 |
| 5,217,720 | 6/1993 | Sekigawa et al. | 424/480 |
| 5,283,064 | 2/1994 | Suzuki et al. | 424/451 |
| 5,330,759 | 7/1994 | Pagay et al. | 424/462 |
| 5,536,507 | 7/1996 | Abramowitz et al. | 424/479 |
| 5,541,170 | 7/1996 | Rhodes et al. | 514/166 |
| 5,541,171 | 7/1996 | Rhodes et al. | 514/166 |
| 5,656,290 | 8/1997 | Kelm et al. | 424/456 |

FOREIGN PATENT DOCUMENTS

| | | | |
|---|---|---|---|
| 839-625 | 7/1976 | Belgium . | |
| 0 040590 | 11/1981 | European Pat. Off. | A61K 9/22 |
| 0225189 | 11/1986 | European Pat. Off. | A61K 9/48 |
| 0251459 | 7/1988 | European Pat. Off. | A61K 9/22 |
| 0313845 | 9/1988 | European Pat. Off. | A61K 9/32 |
| 0 366621 | 5/1990 | European Pat. Off. | A61K 9/54 |
| 2 419722 | 12/1979 | France | A61K 9/58 |
| 53-133-625 | 11/1978 | Japan | A61K 9/36 |
| 57-099521 | 6/1982 | Japan | A61K 31/44 |
| 63-20409 | 6/1982 | Japan . | |
| 59-139317-A | 8/1984 | Japan | A61K 9/64 |
| 59-193816 | 11/1984 | Japan . | |
| 61-221117 | 10/1986 | Japan . | |
| 63-258815-A | 10/1988 | Japan | A61K 31/44 |
| 01117826-A | 5/1989 | Japan | A61K 9/48 |
| 2151921 | 7/1985 | United Kingdom | A61K 9/26 |
| WO 83/00435 | 2/1983 | WIPO | A61K 9/32 |
| WO 91/07172 | 5/1991 | WIPO | A61K 9/22 |
| WO 91/16042 | 10/1991 | WIPO | A61K 9/24 |

(List continued on next page.)

OTHER PUBLICATIONS

U.S. application No. 08/442914, Kelm et al., filed May 17, 1995, Co–pending P&G Case 5672 "Bisacodyl Dosage Form with Multiple Enteric Polymer Coatings for Colonic Delivery".

U.S. application No. 08/442,920, Kelm et al., filed May 17, 1995, Co–pending P&G Case 5674 "Pharmaceutical Dosage Forms with Multiple Enteric Coatings for Colonic Delivery".

Schmidt, P.C., "The MiniWiD–Coater: II. Comparison of Acid Resistance of Enteric–Coated Bisacodyl Pellets Coated With Different Polymers," Drug Development & Industrial Pharmacy, vol. 18, No. 18 (1992), pp. 1969–1979.

Luce, G.T., "Disintegration of tablets enteric coated with cellulose acetate phthalate," Pharm. Tech., vol. 2 (Oct. 1978), pp. 51–55.

Spitael, J., et al. "Enteric Coating using cellulose acetate phthalate", Manuf. Chem., vol. 57, No. 8 (Aug. 1986), pp. 35,37.

(List continued on next page.)

Primary Examiner—Thurman K. Page
Assistant Examiner—William E. Benston, Jr.
Attorney, Agent, or Firm—John M. Howell; Betty J. Zea; Jacobus C. Rasser

[57] ABSTRACT

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutically active agent incorporated into a compressed, bi-convex tablet, with a maximum diameter of about 4 mm to about 10 mm;

b. a non-pH dependent smoothing coat applied to the tablet to provide a smooth tablet surface free from edges or sharp curves; and c. an enteric polymer coating material comprising at least one inner coating layer and only one outer coating layer;

wherein the therapeutically active agent is released at a point near the inlet to, or within the colon; each of the inner coating layer(s) is an enteric polymer that begins to dissolve in an aqueous media at a pH between about 5 to about 6.3; and the outer coating layer is an enteric polymer that begins to dissolve in an aqueous media at a pH between about 6.8 to about 7.2.

17 Claims, No Drawings

FOREIGN PATENT DOCUMENTS

| | | | |
|---|---|---|---|
| WO 93/09767 | 5/1993 | WIPO | A61K 9/54 |
| WO 94/18973 | 9/1994 | WIPO | A61K 31/44 |
| WO 95/30422 | 11/1995 | WIPO | A61K 31/71 |
| WO 96/36321 | 11/1996 | WIPO | A61K 9/50 |
| WO 96/36322 | 11/1996 | WIPO | A61K 9/48 |
| WO 98/16229 | 4/1998 | WIPO | A61K 31/44 |

OTHER PUBLICATIONS

Kane, Y. et al. "Technological evaluation of three enteric coating polymers. Part I. With an insoluble drug," Drug Dev. Ind. Pharm., vol. 19, No. 16 (1993), pp. 2011–2020.

Luce, G.T., "Disintegration of tablets enteric coated with CAP (cellulose acetate phthalate)," Manuf. Chem. Aerosol News, vol. 49, No. 50 (1978), pp. 50, 52, 67.

Preston, D.M., "Pelvic Motility and Response to Intraluminal Bisacodyl in Slow–Transit Constipation," Digestive Diseases & Sciences, vol. 30, No. 4 (1985), pp. 289–294.

Kamm, M.A. et al., "Dynamic scanning defines a colonic defect in severe idiopathic constipation," Gut, vol. 29 (1988), pp. 1085–1092.

Jauch, R. et al., "Bis–(p–hydroxyphenyl)–pyridyl–2–methane: The Common Laxative Principle of Bisacodyl and Sodium Picosulfate," Arzneim.–Forsch. (Drug Res.), vol. 25, No. 11 (1975), pp. 1796–1800.

Roth, W., "Translation of Pharmacokinetics and Laxative Effect of Bisacodyl After Administration of Various Dosage Forms," Arzneim.–Forsch./Drug Res., vol. 38(I), No. 4 (1988), pp. 570–574.

Leng–Peschlow, E., "Effects of Sennosides A+B and Bisacodyl on Rat Large Intestine," Pharmacology, vol. 38 (1989), pp. 310–318.

Rasmussen, S., "Intestinal Absorption of Quinine from Enteric Coated Tablets," Acta Pharmacol. el Toxicol vol. 24 (1966) pp. 331–345.

PHARMACEUTICAL DOSAGE FORM WITH MULTIPLE ENTERIC POLYMER COATINGS FOR COLONIC DELIVERY

This is a continuation-in-part of application Ser. No. 08/442,920, filed May 17, 1995, now U.S. Pat. No. 5,686,105, and a continuation-in-part of application Ser. No. 08/442,914, filed on May 17, 1995, now U.S. Pat. No. 5,656,290, which is a continuation-in-part of application Ser. No. 08/279,361 filed Jul. 22, 1994, abandoned which is a continuation of application Ser. No. 08/023,412, filed Feb. 26, 1993 abandoned.

TECHNICAL FIELD

The present invention relates to novel spherical unit dosage forms to release therapeutic agents at a point near the inlet to, or within the colon.

BACKGROUND OF THE INVENTION

Release of therapeutically active agents in the colon from a perorally administered dosage form is desirable in several situations, including: (1) topical treatment of diseases of the colon such as constipation, irritable bowel syndrome (IBS), Crohn's disease, ulcerative colitis, carcinomas, and infection in which systemic absorption of the therapeutic agent is neither required or desired; (2) systemic absorption of therapeutic agents such as peptides and proteins which are subject to lumenal degradation in the stomach and small intestine; and (3) systemic absorption of therapeutic agents for which peak systemic concentrations and pharmacological activity are desired at time significantly delayed from the time of peroral administration (i.e., peak plasma concentrations in the early morning just prior to arising, from a peroral dosage form ingested at bedtime). Colonic release of therapeutically active agents from a perorally administered dosage form requires that release of said agent for topical activity or systemic absorption be prevented in the stomach and small intestine, but permitted in the colon. This in turn requires design of the dosage form to be such that it takes advantage of features of the gastrointestinal tract that indicate arrival of the dosage form in the colon, relative to other portions of the gastrointestinal tract (M. Ashford and J. T. Fell, *J. Drug Targeting*, 1994, 2:241–258). Variable features include pH, ionic strength, apparent velocity, and bacterial content of the lumenal contents of the several anatomical portions of the gastrointestinal tract as well as the residence time of a pharmaceutical unit dosage form therein (M. Ashford and J. T. Fell, *J. Drug Targeting*, 1994, 2:241–258; S. S. Davis, *J. Contr. Rel.*, 1985, 2:27–38).

The residence time of pharmaceutical unit dosage forms in the stomach can be particularly variable (M. Ashford and J. T. Fell, *J. Drug Targeting*, 1994, 2:241–258). However, the small intestinal transit time of pharmaceutical unit dosage forms has been demonstrated to be relatively constant with a mean value of approximately three hours (M. Ashford and J. T. Fell, *J. Drug Targeting*, 1994, 2:241–258). Residence times in the colon are usually longer than in other portions of the gastrointestinal tract, but times within the several segments can be highly variable (M. Ashford and J. T. Fell, *J. Drug Targeting*, 1994, 2:241–258).

The pH profile of the lumenal contents of the gastrointestinal tract has also been characterized and found to be relatively consistent (D. F. Evans, G. Pye, R. Bramley, A. G. Clark, and T. J. Dyson, *Gut*, 1988, 29:1035–1041). The pH of the stomach may vary temporarily with prandial state, but is generally below about pH 2. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon.

A distinguishing feature of the colon relative to other portions of the gastrointestinal tract is the presence of exogenous bacteria. These are capable of enzymatically catalyzing reactions of which the host animal is incapable.

It has been recognized in general that dosage forms designed for colonic release may employ one of the following features to indicate arrival of the dosage form in the colon, relative to other portions of the gastrointestinal tract: (1) the generally increasing pH profile of the lumenal contents up to the ileocecal junction; (2) the relatively constant small intestinal transit time of a pharmaceutical unit dosage form (compensating for the highly variable stomach residence time); and (3) the presence of exogenous bacteria in the colon (M. Ashford and J. T. Fell, *J. Drug Targeting*, 1994, 2:241–258).

Dosage forms employing the generally increasing pH profile of the lumenal contents of the gastrointestinal tract as a design feature to indicate colonic arrival typically employ film coatings of enteric polymers. These enteric polymers are polyanionic polymers which are insoluble in water and at low pHs, but begin to dissolve at pHs of about 5. Commercially available enteric polymers begin to dissolve within the pH range of about 5 to 7.

The following references use this type of rationale to design dosage forms for delivery to the colon. U.S. Pat. No. 5,171,580, issued Dec. 15, 1992, Boehringer Ingelheim Italia, teaches a preparation for delivery in the large intestine and especially the colon, comprising an active containing core coated with three protection layers of coatings having different solubility. The inner layer is Eudragit® S, with a coating thickness of about 40–120 microns, the intermediate coating layer is a swellable polymer with a coating thickness of about 40–120 microns, and the outer layer is cellulose acetate phthalate, hydroxypropyl methyl cellulose phthalate, polyvinyl acetate phthalate, hydroxyethyl cellulose phthalate, cellulose acetate tetrahydrophthalate, or Eudragit®L. In the dosage forms of the present invention Eudragit®S is only used as an outer layer.

U.S. Pat. No. 4,910,021, issued on Mar. 20, 1990, Scherer Corp., teaches a targeted delivery system wherein the composition comprises a hard or soft gelatin capsule containing an active ingredient such as insulin and an absorption promoter. The capsule is coated with a film forming composition being sufficiently soluble at a pH above 7 as to be capable of permitting the erosion or dissolution of said capsule. The film forming composition is preferably a mixture of Eudragit®L, Eudragit®RS, and Eudragit®S at specific ratios to provide solubility above a pH of 7.

U.S. Pat. No. 4,432,966, issued on Feb. 21, 1984, Roussel-UCLAF, teaches a compressed tablet with an active agent, coated with a first coating layer comprising a mixture of microcrystalline cellulose and lower alkyl ether of a cellulose film-forming organic polymer such as ethyl cellulose, and a second coating layer selected from cellulose acetylphthalate, hydroxypropyl methylcellulose phthalate, benzophenyl salicylate, cellulose acetosuccinate, copolymers of styrene and of maleic acid, formulated gelatin, salol, keratin, stearic acid, myristic acid, gluten, acrylic and methacrylic resins, and copolymers of maleic acid and phthalic acid derivatives.

Using pH as an indicator of colonic arrival of the dosage form presents some difficulties. Although the pH of the lumenal contents gradually increases from the stomach through the small intestine, the pH of the lumenal contents of the proximal portions of the colon is lower than that of the distal small intestine (ileum). This is due to the presence of short chain fatty acids produced by the action of exogenous bacteria in the colon. Therefore, a given pH value does not distinguish the colon from various portions of the small intestine. A dosage form designed to release the therapeutic agent at the pH of the proximal colon would also release the therapeutic agent at those portions of the small intestine proximal to the ileum within which the pH is similar to that of the proximal colon. Thus, the validity of the use of enteric coatings to attain colonic release has been questioned (M. Ashford and J. T. Fell, *J. Drug Targeting*, 1994, 2:241–258; M. Ashford, J. T. Fell, D. Attwood, and P. J. Woodhead, *Int. J. Pharm.*, 1993, 91:241–245; M. Ashford, J. T. Fell, D. Attwood, H. L. Sharma, and P. J. Woodhead, *Int. J. Pharm.*, 1993, 95:193–199)

Although lumenal content pH alone does not distinguish the colon from various other portions of the small intestine, pH does distinguish the stomach from the small intestine and colon. Enteric polymer coatings have been extensively used in the prior art to distinguish the stomach from the small intestine and prevent release of a therapeutic agent until the dosage form has emptied from the stomach. This use has resulted in an extensive history confirming the safety of these polymers, a large literature describing suitable processes for application of these polymers as coatings to dosage forms, and the commercial availability of a number of suitable enteric polymers.

It has been recognized that dosage forms that delay release of a therapeutic agent for a time period corresponding to the stomach and small intestine residence times will provide colonic delivery (S. S. Davis, *J. Contr. Rel.*, 1985, 2:27–38). This has been primarily based upon the reasonably constant residence time in the small intestine, assuming that the additional use of an enteric polymeric coating will compensate for variable stomach residence times by preventing activation of the time based delay mechanism until the dosage form has reached the small intestine. Proposed time delay mechanisms have been based upon slow dissolution of pH independent coatings (A. Gazzaniga, P. Iamartino, G. Maffione, and M. E. Sangalli, Proceed. 6th Int. Conf. on Pharm. Techn. (Paris) 305–313, 1992), controlled pH independent, permeation of water through a coating to activate disintegration of the dosage form by osmotic pressure (F. Theeuwes, P. L. Wong, T. L. Burkoth, and D. A. Fox, in Colonic Drug Absorption and Metabolism, P. R. Bieck, ed., Marcel Dekker, Inc., New York, Basel, Hong Kong, 137–158 (1993)) or by physical swelling (R. Ishino, H. Yoshino, Y. Kirakawa, and K. Noda, *Chem. Pharm. Bull.*, 1992, 40:3036–3041), or swelling and ejection of a plug by pH independent hydration (I. R. Wilding, S. S. Davis, M. Bakhshaee, H. N. E. Stevens, R. A. Sparrow, and J. Brennan, *Pharm. Res.*, 1992, 9:654–657). Such approaches have not been completely satisfactory for reasons of size, reproducibility of time to release, complexity, and expense.

Although enteric polymers have a long history of commercial use and inherently compensate for variable stomach residence times, their use to provide a time based delay in therapeutic agent release based upon dissolution of an enteric polymer coating has not been advocated. This is presumably due to the variability in enteric polymer dissolution as a function of the varying pH and velocity of the lumenal contents of the small intestine and colon. However, a dosage form employing an enteric polymer to achieve colonic release based upon dissolution time of the enteric polymer coating has advantages in terms of proven safety of these polymers and commercially feasible application processes.

It is an object of the present invention to provide colonic release of therapeutic agents from a unit dosage form by employing distinct, multiple coatings or layers of enteric polymers as the means of delaying release of the therapeutic agent until the dosage form has reached the proximal colon.

SUMMARY OF THE INVENTION

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutically active agent incorporated into a compressed, bi-convex tablet, with a maximum diameter of about 4 mm to about 10 mm;

b. a non-pH dependent smoothing coat applied to the tablet to provide a smooth tablet surface free from edges or sharp curves; and c. an enteric polymer coating material comprising at least one inner coating layer and only one outer coating layer;

wherein the therapeutically active agent is released at a point near the inlet to, or within the colon; each of the inner coating layer(s) is an enteric polymer that begins to dissolve in an aqueous media at a pH between about 5 to about 6.3; and the outer coating layer is an enteric polymer that begins to dissolve in an aqueous media at a pH between about 6.8 to about 7.2.

DETAILED DESCRIPTION OF THE INVENTION

The use of enteric polymers to delay release of a therapeutic agent from a pharmaceutical unit dosage form until said dosage form has reached the colon has not been entirely successful. Reasons for the lack of success include:

a. the decrease in the pH of the lumenal contents of the proximal colon relative to the terminal small intestine (ileum) which oviates the use of pH as a recognition factor for colonic delivery as described previously;

b. the difficulty of designing an enteric polymer coating over a unit dosage form that will completely dissolve during the residence time of the dosage form in the small intestine due to the variation in pH and velocity of the lumenal contents of the small intestine and colon; and c. thin spots in the enteric polymer coating that develop over edges and sharp curves in conventional unit dosage forms resulting in premature rupture of the enteric polymer coating and release of the therapeutic agent.

The enteric polymer coated dosage forms of the present invention are designed to delay release of the therapeutic agent for a period of time approximately corresponding to the residence time in the small intestine, rather than employing a given pH value as a recognition factor for colonic arrival. This eliminates the problem introduced by the decrease in pH in the proximal colon relative to the ileum.

The inventors have discovered that the amounts and types of enteric polymers required to delay release of the therapeutic agent for a time approximately corresponding to the residence time in the small intestine can be determined by 1.

a knowledge of the dissolution behavior of the selected enteric polymer as a function of the size of the dosage form and the pH and velocity of an aqueous medium, and 2. by an estimation of the pH and apparent velocity of the lumenal contents of the sequential anatomical segments of the small intestine and colon. Since final dissolution of the enteric coating is desired to occur in the colon, the enteric polymer or polymers comprising the coating of the unit dosage form must be selected and applied to the dosage form such that the coating will be soluble when the dosage form is in the proximal portion of the colon, or at a maximum pH of about 6.3. If a single enteric polymer coating is used, the amounts of enteric polymer required to achieve the requisite delay in release of the therapeutic agent are relatively large. (See P&G Copending patent application Ser. No. 08/442,921, Kelm and Manring, filed on May 17, 1995.) However, the total amount of enteric polymer coating required to achieve colonic release can be reduced if distinct, multiple enteric polymer coating layers are used. The outermost layer consists of an enteric polymer that begins to dissolve at about pH 6.8 to 7.2 in an amount such that this coating layer is completely dissolved within the distal portion of the small intestine (ileum). The inner coating layer(s) consists of enteric polymers that begin to dissolve at about pH 5.0 to 6.3 in an amount such that substantially complete dissolution occurs within the proximal colon. Thus, the function of the outermost coating layer is to prevent release of the therapeutic agent as the dosage form transits the gastrointestinal tract to the distal small intestine, and the function of the inner coating layer(s) is to further delay release of the therapeutic agent until the dosage form has reached the proximal colon.

It is desirable that the enteric polymer coatings essentially completely dissolve prior to release of the therapeutic agent. This assures that the predicted dissolution time for given amounts of enteric polymer coatings corresponds to the time of release of the therapeutic agent. This requires uniform enteric polymer film coating thicknesses over the dosage forms. Thin spots in the enteric polymer coatings can occur over edges and sharp curves of conventional dosage forms (i.e. conventional compressed bi-convex tablets) and can result in premature rupture of the enteric polymer coating and premature release of the therapeutic agent. Therefore, dosage forms of the present invention are spherical or elliptical in shape, of a nearly uniform size, with smooth surfaces essentially free from edges or sharp curves, in order to facilitate the application of a enteric polymer coating of uniform thickness over each of the unit dosage forms.

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutically active agent incorporated into a compressed, bi-convex tablet, with a maximum diameter of about 4 mm to about 10 mm;

b. a non-pH dependent smoothing coat applied to the tablet to provide a smooth tablet surface free from edges or sharp curves; and c. an enteric polymer coating material comprising at least one inner coating layer and only one outer coating layer;

wherein the therapeutically active agent is released at a point near the inlet to, or within the colon; each of the inner coating layer(s) is an enteric polymer that begins to dissolve in an aqueous media at a pH between about 5 to about 6.3; and the outer coating layer is an enteric polymer that begins to dissolve in an aqueous media at a pH between about 6.8 to about 7.2.

The dosage forms of the present invention are to be distinguished from controlled (sustained) release compositions which slowly release a therapeutic agent over an extended period of time and extend the duration of therapeutic action over that achieved with conventional delivery. The dosage forms of the present invention prevent the release of the drug active until the dosage form approximately reaches the colon. The subsequent rate of release of the therapeutic agent after arrival in the colon or near the inlet to the colon, will vary from rapid to slow depending upon the pharmacodynamic requirements of the specific therapeutic agent.

Preferably, the enteric polymer coating material has one inner coating layer and one outer coating layer.

THERAPEUTICALLY ACTIVE AGENT

The methods and dosage formns of the present invention comprise a safe and effective amount of therapeutically active agent. The phrase "safe and effective amount", as used herein, means an amount of therapeutically active agent high enough to provide a significant positive modification of the condition to be treated, but low enough to avoid serious side effects (at a reasonable benefit/risk ratio), within the scope of sound medical judgment. A safe and effective amount of therapeutically active agent will vary with the particular condition being treated, the age and physical condition of the patient being treated, the severity of the condition, the duration of the treatment, the nature of concurrent therapy, the agent selected and like factors.

Therapeutic agents suitable for incorporation into dosage forms of the present invention are those for which release in the colon is therapeutically advantageous. These include therapeutic agents useful for topical treatment of diseases of the colon such as constipation, diarrhea, irritable bowel syndrome (IBS), Crohn's disease, ulcerative colitis, carcinomas, and infection in which systemic absorption of the therapeutic agent is neither required or desired. These include laxatives such as picosulfate and sennosides, anti-diarrheals such as loperamide, nonsteroidal anti- inflammatory drugs such as 5-amino salicylic acid, steroids such as hydrocortisone, prednisolone, prednisolone phosphate, prednisolone metasulpho-benzoate sodium, prednisolone sodium phosphate, glucocorticoids such as dexamethazone, antimicrobials and antiparasitic agents such as erythromycin, chloroquine, iodochlorhydroxyquin, disodohydroxyquin, neomycin and tetracyclines, especially those effective against anaerobic microbes such as methotrexate, immunosuppressants such as cyclosporin A, and chemotherapeutics for treatment of carcinomas.

Certain therapeutic agents, particularly peptides and proteins, are subject to lumenal degradation in the stomach and small intestine. The colon may be a preferable site of absorption for such compounds since lumenal enzymatic activity is less in the colon (M. Mackay and E. Tomlinson, in Colonic Drug Absorption and Metabolism, P. R. Bieck, ed., Marcel Dekker, Inc., New York, Basel, Hong Kong, 137–158 (1993)). Peptides and proteins that may exhibit improved systemic bioavailability benefit when released in the colon include calcitonin, insulin, and human growth hormone. In certain cases, the peptide or protein may be formulated with a system than enhances the absorption of the macromolecule (M. Mackay and E. Tomlinson, in Colonic Drug Absorption and Metabolism, P. R. Bieck, ed., Marcel Dekker, Inc., New York, Basel, Hong Kong, 137–158 (1993)).

Colonic release is also desirable for systemic absorption of therapeutic agents for which peak systemic concentrations and pharmacological activity are desired at time significantly delayed from the time of peroral administration (i.e., peak plasma concentrations in the early morning just prior to arising from a peroral dosage form ingested at bedtime). This is particularly advantageous for conditions such as asthma, arthritis, inflammation, coronary infarction, and angina pectoris which are susceptible to diurnal rhythms (B. Lemmer, in Pulsatile Drug Delivery, R. Gurny, H. E. Junginger, and N. A. Pepas, eds, Wissenschaftliche Verlagsgesellschaft mbH, Stuttgart, 11–24 (1993)). Drugs for which daily variations in their effects have been reported in clinical studies include cardiovascular drugs such as beta-blockers (acebutolol, propranolol), calcium channel blockers (verapamil), and ACE inhibitors (enalapril), anticancer drugs such as cisplatin and doxorubicin, antiasthmatic drugs such as theophylline, minor tranquilizer drugs such as diazepam, $H_1$-antihistamines such as terfenadine, nonsteroidal anti-inflammatory drugs such as ibuprofen, indomethacin, flurbiprofen, naproxen, and piroxicam, and H2-blockers such as cimetidine and ranitidine.

The therapeutically active agent is incorporated in the tablets described herein in a manner consistent with the physical chemical properties of the drug and its pharmacodynamics using techniques known to those skilled in the art. It is recognized that the rate of release of the therapeutically active agent in the colon will be dependent upon the manner of incorporation of the therapeutically active agent and the nature and levels of any excipients. The rate of release should be such that the therapeutic activity of the agent is maximized.

As used herein, "excipient" means any component admixed with or co-incorporated with the therapeutically active agent. Excipients may act to facilitate incorporation of the therapeutically active agent into the substrate, modify the release of the therapeutically active agent from the substrate, stabilize the therapeutically active agent, or enhance absorption of the therapeutically active agent. Excipients should be safe for their intended use at the levels employed in the formulation and compatible with the therapeutically active agent. The formulation of therapeutically active agent and excipients is selected according to criteria well known to those skilled in the art to achieve the desired release rate, stability, absorption, and facilitation of dosage form manufacture.

Pharmaceutical excipients are disclosed in "Remington's Pharmaceutical Sciences", 17th Ed. (1985), pp. 1603–1644, which is herein incorporated by reference. The solids mixture may be prepared via a number of techniques well-known in the pharmaceutical sciences such as dry mixing, wet granulation, and fluid bed granulation, and be incorporated into a compressed, bi-convex tablet, using conventional equipment and processes.

THE DOSAGE FORM AND NON-pH DEPENDENT SMOOTHING COAT

A safe and effective amount of therapeutically active agent is incorporated into a conventional, bi-convex, compressed tablet, with a maximum diameter of about 4 mm to about 10 mm. The conventional, bi-convex, compressed tablet is a tablet compressed by conventional processes, this tablet having a non-smooth surface with edges or sharp curves. However, the application of a safe and effective amount of a non-pH dependent smoothing coat to this tablet, will provide a smooth surface free from edges or sharp curves. This smoothing coat reshapes or rounds out the bi-convex tablet. In addition the application of the non-pH dependent smoothing coat to the bi-convex tablet can provide a spherical and/or elliptical tablet wherein the elliptical tablet has a ratio of the long to short diameters of no greater than about 1.5.

As used herein, "compressed, bi-convex tablet" means a conventional tablet, having a round face, prepared through the compression of a mixture of a therapeutically active agent and pharmaceutical excipients, by two punches, preferably having an identical, spherical standard or deep-concave tooling. Especially preferred tooling is a deep-concave tooling of which the typical axis radius is 3.5 mm for a 5 mm face diameter. Another preferred tooling is a dual radius concave tooling having a smaller axis radius at the face of which the typical ratio is 1/3 to 1/3.5 versus the center axis radius. As indicated above this tablet has a non-smooth surface with edges or sharp curves.

As used herein, "elliptical" means an ellipsoid, a solid figure in which all plane surfaces are approximately ellipses or circles, described by the equation $x^2/a^2+y^2/b^2+z^2/c^2$, wherein $b=c, a/b \leq 1.5$, and "a" is approximately between 4 mm and 10 mm.

As used herein, "smooth surface free from edges or sharp curves" means that, after the application of the smoothing coat, no edges or sharp curves exist on the dosage form sufficient to produce thin spots in the enteric coating relative to the mean enteric coating thickness. Especially preferred dosage forms are conventional tablet forms, having a round face, for example conventional sugar tablets, with a diameter of about 4 mm to about 8 mm; more preferably about 5 mm to about 7 mm. The non-pH dependent smoothing coat, applied to these tablets, will provide a smooth tablet surface free from edges or sharp curves. After application of the smoothing coat, preferably all of the dosage forms are of a uniform size prior to coating with the polymer coating material. Preferably the diameter of every tablet is within about 5%, more preferably within about 2%, of the mean diameter. The smooth surface and uniform size allow for uniform enteric coating thickness and therefore uniform dissolution of the enteric polymer coating material.

The non-pH dependent smoothing coat is any non-enteric polymer coating material or is any inert, water soluble polymer material, known to a skilled artisan. The non-pH dependent smoothing coat preferably is selected from the group consisting of sucrose, Arabic gum, hydroxypropyl cellulose, hydroxypropyl methylcellulose, polyethylene glycol, low viscosity hydroxypropyl cellulose, low viscosity hydroxypropyl methylcellulose, gelatin, sodium alginate, dextrin, psyllium husk powder, and mixtures thereof; more preferably the non-pH dependent smoothing coat is selected from the group consisting of sucrose, Arabic gum, low viscosity hydroxypropyl cellulose, low viscosity hydroxypropyl methylcellulose, gelatin, sodium alginate, dextrin, psyllium husk powder, and mixtures thereof; even more preferably the smoothing coat comprises a mixture of one or more of the above smoothing coat materials with a processing agent selected from the group consisting of talc, lactose, precipitated calcium carbonate, titanium dioxide, silica, microcrystalline cellulose and mixtures thereof, to effectively round or smooth out the compressed core tablet.

The level of the smoothing coat depends on the diameter of the tablet and the size and shape of the tooling used. Preferably the level of the smoothing coat is from about 10% to about 50%, more preferably from about 20% to about 40% of the core tablet weight, even more preferably from about 25% to about 35% of the core tablet weight.

The non-pH dependent smoothing coat may be applied to the compressed, bi-convex tablet by any number of processes well known to those skilled in the art, including, but not limited to, perforated pan coating and fluid bed coating.

The tablet preferably comprises a solid form of therapeutically active agent and is compressed using conventional equipment and processes. Any compressed tablet preferably is made such that it rapidly disintegrates in intestinal juices.

THE ENTERIC POLYMER COATING MATERIAL

In the compositions of the present invention, the polymer coating material prevents the release of therapeutically active agent as the dosage form passes through the upper gastrointestinal tract, including the mouth, esophagus, stomach, and small intestine, until the dosage form is near the junction between the small intestine and the colon or is in the colon. This precludes systemic absorption of therapeutically active agent from the upper gastrointestinal tract and/or dilution of the released therapeutically active agent in the contents of the upper gastrointestinal tract. Therefore, the polymer coating materials, in combination with a rounded, spherical or elliptical compressed tablet with a smooth surface, free of edges or sharp curves, provides a method of delivering the therapeutically active agent in a concentrated form to the colon.

As used herein, "enteric polymer coating material," refers to materials which completely surround and encase the therapeutically active agent in the unit dosage form prior to oral administration. The polymer coating material of the present invention does not contain any active compound, i.e. therapeutically active agent, of the present invention. In addition the present invention does not comprise enteric coated microcrystal spheres, enteric coated particles, or enteric coated granules of the active compound. Preferably, a substantial amount or all of the enteric polymer coating material is dissolved before the therapeutically active agent is released from the dosage form, so as to achieve delayed dissolution of the therapeutically active agent.

The polymer coating materials are selected such that therapeutically active agent will be released at about the time that the dosage form reaches the inlet between the small intestine and the colon, or thereafter in the colon. The selection is based upon the pH profile of the small intestine and colon. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon. In order to provide a predictable dissolution time corresponding to the small intestinal transit time of about 3 hours and permit reproducible release of drug at the inlet between the small intestine and the colon, or thereafter in the colon, the coating should begin to dissolve within the pH range of the small intestine and continue to dissolve at the pH of the proximal colon. This means that a single coating layer of a single enteric polymer coating material should begin to dissolve in the pH range of about 5 to 6.3, which requires a minimum coating thickness of 250 µm. (See P&G Copending patent application Ser. No. 08/442,921, Kelm and Manring, filed on May 17, 1995.) Single layer coatings of enteric polymer coating materials which begin to dissolve at higher pH levels, such as about 7, require less coating thickness for the dosage form to reach the inlet between the small intestine and the colon, or the colon. However, any coating remaining when the dosage form reaches the colon will not dissolve in the proximal portions of the colon where the pH is less than 7, thus delaying drug release until the dosage form has reached a portion of the colon where the lumenal pH is greater than 7.

In order to provide for release in the proximal colon while minimizing total enteric polymer coating thickness, the enteric polymer coating materials of the present invention consist of a sequential coating of multiple, preferably two, materials in distinct, multiple layers. The outer coating layer consists of an enteric polymer coating material which begins to dissolve at a pH between about 6.8 to about 7.2 in an amount such that this layer is completely dissolved when the dosage form is in the distal small intestine. The inner layer, or layers, consist(s) of enteric polymer coating material(s) that begin to dissolve at pHs between about 5 to about 6.3, preferably a pH between about 5 to about 6, more preferably a pH between about 5 to about 5.5. The amount(s) of the inner layer(s) is(are) such that release of the drug is delayed until the dosage form has reached the inlet between the small intestine and the colon, or the colon. Thus, the function of the outer coating layer of enteric polymer coating material is to prevent release of the drug from the stomach through to the distal portion of the small intestine, and the function of the inner coating layer(s) is to prevent release of the drug from the distal portion of the small intestine (from the time the outermost layer has dissolved) to the inlet between the small intestine and the colon, or the colon.

Preferred coating materials for the outer coating layer of enteric polymer coating material include pH-sensitive materials, which remain intact in the lower pH environs of the stomach and small intestine, but begin to dissolve in an aqueous solution at a pH between about 6.8 to about 7.2. The coating thickness is dependent upon the size of the unit dosage form, but ranges from about 20 µm to about 50 µm. Preferred materials for the outer coating layer of enteric polymer coating material are poly(methacrylic acid, methyl methacrylate) 1:2 (Eudragit® S), and mixtures of poly (methacrylic acid, methyl methacrylate) 1:1 (Eudragit® L) and poly(methacrylic acid, methyl methacrylate) 1:2 (Eudragit® S) in a ratio of about 1:10 to about 1:2, preferably about 1:5 to about 1:3. Especially preferred is Eudragit® S.

Eudragit® L, is an anionic copolymer derived from methacrylic acid and methyl methacrylate, with a ratio of free carboxyl groups to the ester groups of approximately 1:1, and a mean molecular weight of approximately 135,000, from Rohm Tech; Eudragit® S is an anionic copolymer derived from methacrylic acid and methyl methacrylate, with a ratio of free carboxyl groups to the ester groups of approximately 1:2, and a mean molecular weight of approximately 135,000, from Rohm Tech.

Preferred coating materials for the inner coating layer(s) include pH-sensitive materials, which remain intact in the lower pH environs of the stomach and small intestine, but which disintegrate or dissolve at the pHs commonly found in the distal portion of the small intestine and especially, in the proximal colon. The inner coating layer polymers have a low apparent pKa range to minimize the impact of the drop in the pH across the ileo-cecal valve. The inner coating layer enteric polymer(s) begins to dissolve in an aqueous solution at a pH between about 5 to about 6.3. It is particularly important that the enteric polymer(s) be soluble in the proximal portion of the colon where the lumenal pH is typically lower than that in the distal portions of the small intestine. This lower pH is due to the presence of short chain fatty acids produced by the metabolic activity of bacteria residing in the colon.

The enteric polymer coating materials for the inner layer(s) are selected from the group consisting of cellulose acetate phthalate; cellulose acetate trimelliate; hydroxypropyl methylcellulose phthalate; hydroxypropyl methylcellulose acetate succinate; polyvinyl acetate phthalate; poly(methacrylic acid, methyl methacrylate) 1:1; poly(methacrylic acid, ethyl acrylate) 1:1; and compatible mixtures thereof, preferably poly(methacrylic acid, methyl methacrylate) 1:1 and poly(methacrylic acid, ethyl acrylate) 1:1, and compatible mixtures thereof, more preferably poly(methacrylic acid, ethyl acrylate) 1:1.

Specific examples of these polymer coating materials include the following: Eudragit® L, an anionic copolymer derived from methacrylic acid and methyl methacrylate, with a ratio of free carboxyl groups to the ester groups of approximately 1:1, and a mean molecular weight of approximately 135,000;

Eudragit® L 30 D, an aqueous acrylic resin dispersion, an anionic copolymer derived from methacrylic acid and ethyl acrylate with a ratio of free carboxyl groups to the ester groups of approximately 1:1, and a mean molecular weight of approximately 250,000; (it is supplied as an aqueous dispersion containing 30% w/w of dry lacquer substance);

Eudragit® L 100-55, an anionic copolymer derived from methacrylic acid and ethyl acrylate, with a ratio of free carboxyl groups to the ester groups of approximately 1:1, and a mean molecular weight greater than about 100,000;

cellulose acetate phthalate or CAP®, available from Eastman Chemical; cellulose acetate trimelliate, CAT® available from Eastman Chemical; hydroxypropyl methylcellulose phthalate (USP/NF type 220824) HPMCP 50® and (USP/NF type 200731) HPMCP 55® available from Shin Etsu Chemical; polyvinyl acetate phthalate, PVAP®, available from Colorcon; hydroxypropyl methylcellulose acetate succinate, HPMCAS®, available from Shin Etsu Chemical.

A preferred polymer coating material is poly(methacrylic acid, ethyl acrylate) 1:1 (Eudragit® L 100-55), wherein for diameters of about 4 to about 7 mm, the preferred coating thickness is about 120 to 350 μm and about 100 to 300 μm, respectively.

Another preferred polymer is poly(methacrylic acid, methyl methacrylate) 1:1 (Eudragit® L), wherein for diameters of about 4 to about 7 mm, the preferred coating thicknesses is about 110 to 300 μm and about 90 to 250 μm, respectively.

The total amount of enteric polymer coatings on the dosage form must be sufficient such that complete dissolution of the coating does not occur until the dosage form is at a location within the gastrointestinal tract near the opening to, or within the colon, thereby releasing therapeutically active agent in the colon. This requires a rounded, spherical or elliptical dosage form, free from surface edges or sharp curves which will produce thin spots in the coatings. The coatings over such thin spots will dissolve prior to the dosage form reaching the colon, resulting in premature release of therapeutically active agent.

Transit of pharmaceutical dosage forms through the gastrointestinal tract has been characterized in the literature (i.e., M. Ashford and J. T. Fell, *J. Drug Targeting*, 1994, 2:241–258). Gastric emptying of pharmaceutical dosage forms can be highly variable, but transit through the small intestine is relatively constant with a mean transit time of about three hours. The pH-solubility behaviors of the enteric polymers of the present invention are such that significant dissolution of the enteric polymer coating will not occur until the dosage form has emptied from the stomach, thereby eliminating the variability of gastric emptying as a factor in determining the amount of coating required to achieve release of therapeutically active agent in the colon. Therefore, the amount of enteric polymer coating should be such that it is substantially dissolved during the approximate three hour transit time of the small intestine.

Dissolution of the enteric polymers of the present invention is influenced by the size of the dosage form, and the pH, ionic strength, and velocity of the surrounding aqueous medium. The latter three factors vary throughout the length of the small intestine and colon. In addition, the effect of these factors upon dissolution rate varies with each enteric polymer. However, the amount of a single coating layer of enteric polymer is substantial, wherein the enteric polymer is soluble in the proximal portions of the colon, as taught in P&G Copending patent application Ser. No. 08/442,921, Kelm and Manring, filed on May 17, 1995. An important aspect of the present invention is the use of multiple coating layers of enteric polymers in which the outermost layer consists of an enteric polymer or combination of enteric polymers which are insoluble below about pH 6.8. The inner layer(s) consist of enteric polymer(s) that begin to dissolve at a pH between about 5 to about 6.3 in order to be soluble in the proximal portions of the colon. The use of multiple layers in the manner described herein reduces the total amount of enteric polymer coating relative to the use of a single coating layer of enteric polymer that is soluble in the proximal portions of the colon.

The more important parameters for determination of the amount of enteric polymer required to delay drug release until the dosage form has reached the colon have been found to include the pH solubility profiles of the enteric polymers employed in the outermost and inner coating layers and the size of the dosage form. Approximate minimum amounts of enteric polymer as a function of the pH at which the polymer begins to dissolve and dosage form size are shown in the following table, Table 1. Also included are examples of enteric polymers.

TABLE 1

| Diameter (mm) | Layer | pH | Minimum Thickness (μm) | Example Enteric Polymers |
| --- | --- | --- | --- | --- |
| 3 | Inner | 5.0 | 150 | HPMCP 50 |
| 3 | Outer | 7.0 | 40 | Eudragit ® S |
| 5 | Inner | 5.0 | 130 | HPMCP 50 |
| 5 | Outer | 7.0 | 30 | Eudragit ® S |
| 10 | Inner | 5.0 | 100 | HPMCP 50 |
| 10 | Outer | 7.0 | 20 | Eudragit ® S |
| 3 | Inner | 5.5 | 140 | Eudragit ®L100-55 |
| 3 | Outer | 7.0 | 40 | Eudragit ® S |
| 5 | Inner | 5.5 | 120 | Eudragit ®L100-55 |
| 5 | Outer | 7.0 | 30 | Eudragit ® S |
| 10 | Inner | 5.5 | 90 | Eudragit ®L100-55 |
| 10 | Outer | 7.0 | 20 | Eudragit ® S |
| 3 | Inner | 6.0 | 130 | Eudragit ® L |
| 3 | Outer | 7.0 | 40 | Eudragit ® S |
| 5 | Inner | 6.0 | 110 | Eudragit ® L |
| 5 | Outer | 7.0 | 30 | Eudragit ® S |
| 10 | Inner | 6.0 | 80 | Eudragit ® L |
| 10 | Outer | 7.0 | 20 | Eudragit ® S |

The enteric polymer coating material may by applied to the rounded, spherical, or elliptical dosage form as a solution in a pharmaceutically acceptable solvent such as ethanol, acetone, isopropanol, ethyl acetate, or mixtures thereof; as an aqueous solution buffered with ammonium hydroxide; or as a fine dispersion in water using any number of processes known to one skilled in the art, including but not limited to, perforated pan coating and fluid bed coating.

To enhance the elasticity of the coating materials, preferably the coating material of the present invention also comprises a plasticizer. Appropriate plasticizers include polyethylene glycols, propylene glycols, dibutyl phthalate, diethyl phthalate, tributyl citrate, tributyrin, butyl phthalyl butyl glycolate (Santicizer® B-16, from Monsanto, St. Louis, Mo.), triacetin, castor oil and citric acid esters; preferably the plasticizer is dibutyl phthalate or triethyl citrate. These plasticizers are present in an amount to facilitate the coating process and to obtain an even coating film with enhanced physical stability. Generally the coating material comprises from about 0% to about 50% of a plasticizer, preferably from about 5% to about 25% by weight, more preferably from about 10% to about 20% by weight of the enteric polymer.

In addition, to facilitate the coating process, the enteric coating material may also comprise inert solid particulates. Preferred inert solid particulates include talc and titanium dioxide.

For the enteric polymer materials, the selections of optional plasticizer, optional inert solid particulate, and levels thereof, coating formulation type (solvent, ammoniated aqueous solution, or aqueous dispersion), and process of coating are based upon the specific enteric polymer used and the type of dosage form used according to criteria known to those skilled in the art.

METHOD OF MAKING

Enteric polymers are generally applied onto the dosage forms as solutions in organic solvents. The solvents commonly employed as vehicles are methylene chloride, ethanol, methanol, isopropyl alcohol, acetone, ethyl acetate and combinations thereof The choice of the solvent is based primarily on the solubility of the polymer, ease of evaporation, and viscosity of the solution.

Some polymers are also available as aqueous systems. Currently, three aqueous enteric polymer coatings are available for commercial use in the United States. These are Eudragit® L30D (methacrylic acid-ethyl acrylate ester copolymer marketed by Rohm-Haas GmBH, West Germany); Aquateric® (cellulose acetate phthalate-containing product marketed by FMC Corporation, Philadelphia, Pa.); and Coateric ® (a polyvinyl acetate phthalate based product marketed by Colorcon, Inc., West Point, Pa.). Unlike organic solutions, these aqueous-based systems can be prepared at high concentration without encountering high viscosity. Also, these aqueous systems do not have the problems associated with the organic systems such as flammability, toxicity of the residual solvent in the dosage form, etc.

Coating can be achieved by methods known to one skilled in the art such as by using fluidized bed equipment, perforated pans, a regular pharmaceutical pan, compression coating, etc. by continuous or short spray methods, or by drenching.

All percentages used herein are by weight of the composition unless otherwise indicated.

The following non-limiting examples provide typical formulations and dosage forms for compositions of the present invention.

EXAMPLE 1

A dosage form of the following formulation is prepared as described below:

| Component | Wt. (mg) | Component | Wt. (mg) |
|---|---|---|---|
| Substrate | | Non-pH Dependent Smoothing Coat | |
| Dextramethasone | 3 | Sucrose | 10 |
| Lactose | 34 | Talc | 6 |
| Corn Starch | 8 | Arabic Gum | 1 |
| Pre-gelatinized Starch | 12 | | |
| HPC-L[1] | 1.7 | | |
| Magnesium Stearate | 0.3 | | |
| Inner Enteric Coat | | Outermost Enteric Coat | |
| Eudragit ® L100-55[2] | 18 | Eudragit ® S100[3] | 5 |
| Dibutyl Phthalate | 4 | Dibutyl Phthalate | 1 |
| Talc, USP | 8 | Red Ferric Oxide | 1 |
| | | Talc, USP | 2 |

[1]Hydroxypropyl Cellulose, Low-substituted, Dow Chemical.
[2]Poly(methacrylic acid, ethyl acrylate) 1:1, Eudragit ® L100-55, Rohm Tech.
[3]Poly(methacrylic acid, methyl methacrylate) 1:2, Eudragit ® S100, Rohm Tech.

Substrate

Dextramethasone, Lactose, Corn Starch, Pre-gelatinized Starch and HPC-L are mixed and wet-granulated by a fluid-bed Granulator. Then, the granules are blended with magnesium stearate in a V-blender and compressed into biconvex tablet with 5 mm diameter.

Non-pH Dependent Smoothing Coat

Arabic gum is dissolved in warm purified water and sucrose is dissolved in this solution. Then, talc is suspended in this Arabic-gum/sucrose solution to produce a 74% by weight syrup which is coated on the substrates described above in either a perforated pan coater or conventional pan coater maintaining an outlet air/bed temperature of about 45° C.

Inner Enteric Coat

Eudragit® L100-55 and dibutyl phthalate are dissolved in a solution of isopropanol, acetone, and water (37:9:1) at levels of 8.0% and 1.6% (total weight percent), respectively. Talc is then suspended in the solution at a levels of 3.3% by weight. The resulting mixture is coated onto the smooth coated substrates above in a perforated pan coater maintaining an outlet air/bed temperature of about 30° C.

Outermost Enteric Coat

Eudragit® S100 and dibutyl phthalate are dissolved in a solution of isopropanol, acetone, and water (37:9:1) at levels of 8.0% and 1.6% (total weight percent), respectively. Red ferric oxide and talc are then suspended in the solution at levels of 1.2% and 2.1% by weight, respectively. The resulting mixture is coated onto the smooth coated substrates above in a perforated pan coater maintaining an outlet air/bed temperature of about 30° C.

EXAMPLE 2

A dosage form of the following formulation is prepared as described below:

| Component | Wt. (mg) | Component | Wt. (mg) |
|---|---|---|---|
| Substrate | | Non-pH Dependent Smoothing Coat | |
| Propanolol Base | 15 | Sucrose | 10 |
| Lactose | 34 | Talc | 6 |

| Component | Wt. (mg) | Component | Wt. (mg) |
|---|---|---|---|
| Corn Starch | 8 | Arabic Gum | 1 |
| Pre-gelatinized Starch | 12 | | |
| HPC-L[1] | 1.7 | | |
| Magnesium Stearate | 0.3 | | |
| Inner Enteric Coat | | Outermost Enteric Coat | |
| Eudragit ® L100-55[2] | 18 | Eudragit ® S100[3] | 5 |
| Dibutyl Phthalate | 4 | Dibutyl Phthalate | 1 |
| Talc, USP | 8 | Red Ferric Oxide | 1 |
| | | Talc, USP | 2 |

[1]Hydroxypropyl Cellulose, Low-substituted, Dow Chemical.
[2]Poly(methacrylic acid, ethyl acrylate) 1:1, Eudragit ® L100-55, Rohm Tech.
[3]Poly(methacrylic acid, methyl methacrylate) 1:2, Eudragit ® S100, Rohm Tech.

Substrate

Propanolol base, Lactose, Corn Starch, Pre-gelatinized Starch and HPC-L are mixed and wet-granulated by a fluid-bed granulator. Then, the granules are blended with magnesium stearate in a V-blender and compressed into biconvex tablet with 5 mm diameter.

Non-pH Dependent Smoothing Coat

Arabic gum is dissolved in warm purified water and sucrose is dissolved in this solution. Then, talc is suspended in this Arabic-gum/sucrose solution to produce a 74% by weight syrup which is coated on the substrates described above in either a perforated pan coater or conventional pan coater maintaining an outlet air/bed temperature of about 45° C.

Inner Enteric Coat

Eudragite® L100-55 and dibutyl phthalate are dissolved in a solution of isopropanol, acetone, and water (37:9:1) at levels of 8.0% and 1.6% (total weight percent), respectively. Talc is then suspended in the solution at a levels of 3.3% by weight. The resulting mixture is coated onto the smooth coated substrates above in a perforated pan coater maintaining an outlet air/bed temperature of about 30° C.

Outermost Enteric Coat

Eudragit® S100 and dibutyl phthalate are dissolved in a solution of isopropanol, acetone, and water (37:9:1) at levels of 8.0% and 1.6% (total weight percent), respectively. Red ferric oxide and talc are then suspended in the solution at levels of 1.2% and 2.1% by weight, respectively. The resulting mixture is coated onto the smooth coated substrates above in a perforated pan coater maintaining an outlet air/bed temperature of about 30° C.

EXAMPLE 3

A dosage form of the following formulation is prepared as described below:

| Component | Wt. (mg) | Component | Wt. (mg) |
|---|---|---|---|
| Substrate | | Non-pH Dependent Smoothing Coat | |
| Mesalamine (5-amino-2-hydroxybenzoic acid) | 200 | Sucrose | 10 |
| | | Talc | 6 |
| | | Arabic Gum | 1 |
| Lactose | 34 | | |
| Corn Starch | 100 | | |
| Pre-gelatinized Starch | 20 | | |
| HPC-L[1] | 20 | | |
| Magnesium Stearate | 0.3 | | |
| Inner Enteric Coat | | Outermost Enteric Coat | |
| Eudragit ® L[2] | 8 | Eudragit ® S100[3] | 3 |
| Dibutyl Phthalate | 1.6 | Dibutyl Phthalate | 0.6 |
| Talc, USP | 3 | Red Ferric Oxide | 0.5 |
| | | Talc, USP | 1 |

[1]Hydroxypropyl Cellulose, Low-substituted, Dow Chemical.
[2]Poly(methacrylic acid, methyl methacrylate) 1:1, Eudragit ® L, Rohm Tech.
[3]Poly(methacrylic acid, methyl methacrylate) 1:2, Eudragit ® S100 Rohm Tech.

Substrate

Mesalamine, Lactose, Corn Starch, Pre-gelatinized Starch and HPC-L are mixed and wet-granulated by a fluid-bed granulator. Then, the granules are blended with magnesium stearate in a V-blender and compressed into biconvex tablet with 5-mm diameter.

Non-pH Dependent Smoothing Coat

Arabic gum is dissolved in warm purified water and sucrose is dissolved in this solution. Then, talc is suspended in this Arabic-gum/sucrose solution to produce a 74% by weight syrup which is coated on the substrates described above in either a perforated pan coater or conventional pan coater maintaining an outlet air/bed temperature of about 45° C.

Inner Enteric Coat

Eudragit® L and dibutyl phthalate are dissolved in a solution of isopropanol, acetone, and water (37:9:1) at levels of 8.0% and 1.6% (total weight percent), respectively. Talc is then suspended in the solution at a levels of 3.3% by weight. The resulting mixture is coated onto the smooth coated substrates above in a perforated pan coater maintaining an outlet air/bed temperature of about30° C.

Outermost Enteric Coat

Eudragit® S100 and dibutyl phthalate are dissolved in a solution of isopropanol, acetone, and water (37:9:1) at levels of 8.0% and 1.6% (total weight percent), respectively. Red ferric oxide and talc are then suspended in the solution at levels of 1.2% and 2.1% by weight, respectively. The resulting mixture is coated onto the smooth coated substrates above in a perforated pan coater maintaining an outlet air/bed temperature of about 30° C.

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A pharmaceutical composition in a unit dosage form for peroral administration in a human or lower animal, having a gastrointestinal tract comprising a small intestine and a colon with a lumen therethrough having an inlet to the colon from the small intestine, comprising:
   a. a safe and effective amount of a therapeutically active agent incorporated into a compressed, bi-convex tablet, with a maximum diameter of about 4 mm to about 10 mm;
   b. a non-pH dependent smoothing coat applied to the tablet to provide a smooth tablet surface free from edges or sharp curves; and
   c. an enteric polymer coating material comprising at least one inner coating layer and only one outer coating layer;

wherein the therapeutically active agent is released at a point near the inlet to, or within the colon; each of the inner coating layer(s) is an enteric polymer that begins to dissolve in an aqueous media at a pH between about 5 to about 6.3; and the outer coating layer is an enteric polymer that begins to dissolve in an aqueous media at a pH between about 6.8 to about 7.2.

2. The composition of claim 1 wherein the level of smoothing coat is from about 10% to about 50% of the core tablet weight.

3. The composition of claim 2 wherein the level of smoothing coat is from about 20% to about 40% of the core tablet weight.

4. The composition of claim 2 wherein the non-pH dependent smoothing coat is selected from the group consisting of sucrose, Arabic gum, hydroxypropyl cellulose, hydroxypropyl methylcellulose, polyethylene glycol, low viscosity hydroxypropyl cellulose, low viscosity hydroxypropyl methylcellulose, gelatin, sodium alginate, dextrin, psyllium husk powder, and mixtures thereof.

5. The composition of claim 4 wherein the non-pH dependent smoothing coat is selected from the group consisting of sucrose, Arabic gum, low viscosity hydroxypropyl cellulose, low viscosity hydroxypropyl methylcellulose, gelatin, sodium alginate, dextrin, psyllium husk powder, and mixtures thereof.

6. The composition of claim 4 wherein the non-pH dependent smoothing coat additionally comprises a processing agent selected from the group consisting of talc, lactose, precipitated calcium carbonate, titanium dioxide, silica, microcrystalline cellulose and mixtures thereof, to effectively round or smooth out the compressed core tablet.

7. The composition of claim 4 wherein the enteric polymer coating material comprises one inner coating layer.

8. The composition of claim 7 wherein the inner coating layer is selected from the group consisting of cellulose acetate phthalate; cellulose acetate trimelliate; hydroxypropyl methylcellulose phthalate; hydroxypropyl methylcellulose acetate succinate; polyvinyl acetate phthalate; poly (methacrylic acid, methyl methacrylate) 1:1; poly (methacrylic acid, ethyl acrylate) 1:1; and compatible mixtures thereof.

9. The composition of claim 8 wherein the inner coating layer is selected from the group consisting of poly (methacrylic acid, methyl methacrylate) 1:1; poly (methacrylic acid, ethyl acrylate) 1:1; and compatible mixtures thereof.

10. The composition of claim 9 wherein the inner coating layer is poly( methacrylic acid, ethyl acrylate) 1:1, which has a coating thickness of about 120 $\mu$m to about 350 $\mu$m when the diameter is about 4 mm.

11. The composition of claim 9 wherein the inner coating layer is poly(methacrylic acid, ethyl acrylate) 1:1, which has a coating thickness of about 100 $\mu$m to about 300 $\mu$m when the diameter is about 7 mm.

12. The composition of claim 9 wherein the inner coating layer is poly(methacrylic acid, methyl methacrylate) 1:1, which has a coating thickness of about 110 $\mu$m to about 300 $\mu$m when the diameter is about 4 mm.

13. The composition ofeclaim 9 wherein the inner coating, layer is poly(methacrylic acid, methyl methacrylate) 1:1, which has a coating, thickness of about 90 $\mu$m to about 250 $\mu$m when the diameter is about 7 mm.

14. The composition of claim 7 wherein the outer coating layer is selected from the group consisting of poly (methacrylic acid, methyl methacrylate) 1:2, and a mixture of poly(methacrylic acid, methyl methacrylate) 1:1 and poly(methactylic acid, methyl methacrylate) 1:2 in a ratio of about 1:10 to about 1:2.

15. The composition of claim 14 wherein the outer coating layer is poly(methacrylic acid, methyl methacrylate) 1:2.

16. The composition of claim 1 wherein the therapeutically active agent is selected from the group consisting of picosulfate, sennosides, anti-diarrheals, nonsteroidal anti-inflammatory agents, glucocorticoids, antimicrobials, immunosuppressants, chemotherapeutics, peptides, proteins, beta blockers, calcium channel blockers, ACE inhibitors, H2-blockers, antiasthmatic agents, and antihistamines.

17. A method for providing delivery of a therapeutically active agent to the colon of a human or lower animal by administering a safe and effective amount of the composition of claim 1 perorally.

* * * * *